US006602511B2

(12) United States Patent
von Corswant

(10) Patent No.: US 6,602,511 B2
(45) Date of Patent: *Aug. 5, 2003

(54) MICROEMULSIONS FOR USE AS VEHICLES FOR ADMINISTRATION OF ACTIVE COMPOUNDS

(75) Inventor: Christian von Corswant, Mölndal (SE)

(73) Assignee: AstraZeneca AB, Sodertalje (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 7 days.

(21) Appl. No.: 08/718,485

(22) PCT Filed: Sep. 4, 1996

(86) PCT No.: PCT/SE96/01097

§ 371 (c)(1),
(2), (4) Date: Sep. 20, 1996

(87) PCT Pub. No.: WO97/09964

PCT Pub. Date: Mar. 20, 1997

(65) Prior Publication Data

US 2001/0007663 A1 Jul. 12, 2001

(30) Foreign Application Priority Data

Sep. 12, 1995 (SE) ............................................. 9503143

(51) Int. Cl.⁷ .......................... A61K 9/107; A61K 9/127
(52) U.S. Cl. ...................... 424/400; 424/450; 514/937; 514/938; 514/941; 514/943
(58) Field of Search ................. 424/400, 450; 514/937–943

(56) References Cited

U.S. PATENT DOCUMENTS

| 4,719,239 A | 1/1988 | Muller et al. ............... 514/785 |
| 5,364,632 A | * 11/1994 | Benita et al. ............... 424/450 |
| 5,658,575 A | 8/1997 | Ribier et al. ............... 424/401 |

FOREIGN PATENT DOCUMENTS

| EP | 0211258 | 2/1985 |
| EP | 0334777 | 9/1989 |
| EP | 0391369 | 10/1990 |
| EP | 0641557 | 3/1995 |
| EP | 0651994 | 5/1995 |
| EP | 0728460 | 8/1996 |
| FR | 2553666 | 10/1983 |
| HU | 9402567 | 7/1995 |
| WO | 9218147 | 10/1992 |
| WO | 9302664 | 2/1993 |
| WO | 9709964 | 3/1997 |

OTHER PUBLICATIONS

K. Shinoda et al. "Lecithin–based microemulsions; Phase Behavior and . . . " 1991 J. Phys.Chem. 95: 989–993.

I. Danielsson et al. "The defintion of microemulsion " 1981 Colloids and Surfaces 3:391–392.

Gallarate et al. "Micro–emulsions containing lecithin and bile salts: evaluation of the role . . . " (1993) STP Pharma Sciences 3: 413–418.

* cited by examiner

Primary Examiner—Gollamudi S. Kishore
(74) Attorney, Agent, or Firm—White & Case LLP

(57) ABSTRACT

A non-toxic oil-in-water or bicontinous microemulsion used as a pharmaceutically acceptable vehicle for administration of one or more active compounds having a low solubility in water as well as a process for the preparation and the use thereof.

22 Claims, 1 Drawing Sheet

Fig 1: Experimental setup for the hemodynamic study.
(6 SPD-rats for each vehicle)
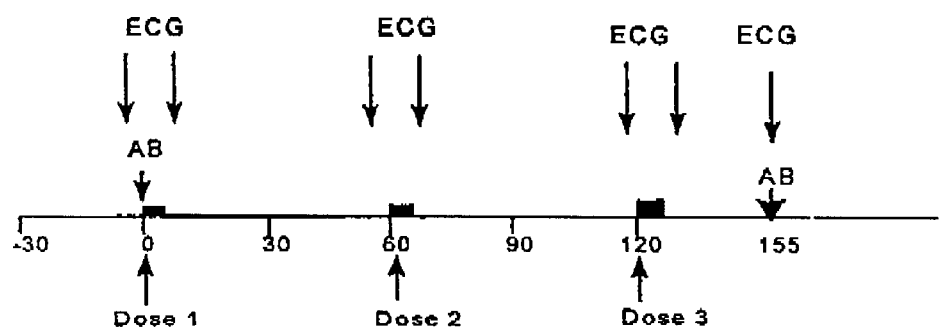
AB=Acid-Base with pH, $pCO_2$, $pO_2$, BE, Hb, Na, K from 100 µl of blood

MICROEMULSIONS FOR USE AS VEHICLES FOR ADMINISTRATION OF ACTIVE COMPOUNDS

This application is a 3718 PCT/SE 96/01097 filed Sep. 4, 1996.

TECHNICAL FIELD

The present invention relates to a microemulsion used as a pharmaceutically acceptable vehicle for administration of one or more active compounds parenterally but also orally and transdermally, as well as a process for the preparation and use of such a microemulsion.

The object of the present invention is to provide a vehicle which increases the solubility of compounds having a low solubility in water at the same time as being non-toxic.

BACKGROUND OF THE INVENTION AND PRIOR ART

Many of the new pharmaceutically active substances which are prepared today have a very low solubility in water. This could be a problem when administered, especially when a substance is to be administered parenterally, e.g. intravenously, intraperitonially, intraarterially, intramuscularly or subcutaneously. In these cases a vehicle which increases the solubility of the active compound is needed. The solubility in water often has to be increased 1000 times to 10 000 times to reach reasonable volumes for administration. The systems used today are;

- solvents which are possible to mix with water, such as propylene glycol, polyethylene glycol, ethanol etc.;
- surfactants forming aggregate in which the unsoluble substances can be dissolved, for example ethoxylated castor oil, mixed micells of lecithin and bile salts;
- polyethylene oxide derivatives of sorbitan monoesters, diesters and triesters;
- complexing agents such as cyclodextrines;
- emulsions, for example soybean oil and egglecithin.

All these systems have different drawbacks. Solvents which are possible to mix with water require high concentrations to be effective. The solubilizing capacity of the surfactants and the complexing agent is often insufficient. Emulsions are thermodynamically unstable and also non-transparent which makes it difficult to decide whether the active substance is completely dissolved or not. Microemulsions are on the contrary, thermodynamically stable mixtures that are formed spontaneously without any addition of external energy, e.g. mechanical stirring, heating, ultrasonification ect. Microemulsions are also transparent which make them superior to ordinary emulsions for use as vehicles for administration of pharmacetically active compounds.

One objective with the present invention is to provide a microemulsion using minimal amounts of surfactants for use as a vehicle suitable for parenteral as well as oral and transdermal administration of one or more pharmaceutically active compounds.

The benefit with a microemulsion is the high solubilization capacity and the fact that it is both thermodynamically stable and translucent. In EP 211 258 a preparation called an "oil-in-water microemulsion" for parenteral administration is described, which consists of pharmaceutically acceptable lipids, lipophilic drugs and mixtures thereof, and a phospholipid emulsifier in an aqueous phase. However, here the microemulsification is achieved by using mechanical energy input, i.e. droplet size reduction via microfluidization. This is not a microemulsion according to usual definition for microemulsions—"a microemulsion is defined as a system of water, oil and amphiphile which is a single optically isotropic and thermodynamically stable liquid solution" (Danielsson, I., Lindman, B., Colloids and Surfaces, 1981, 3, p. 391). An oil-in-water microemulsion for parenteral administration is described in FR 2 553 661. This microemulsion contains an ionic surfactant and an aliphatic polyol or an aromatic alcohol having at least 4 carbon atoms as a co-surfactant. In the example of this specification the ratio of lipophilic phase:surfactant is 1:1. In WO 92/18147 a water-in-oil microemulsion is described which readily converts to an oil-in-water emulsion or microemulsion by the addition of aqueous fluid. This microemulsion contains a hydrophilic water-soluble active substance. However, it is most likely impossible to use as low amount of surfactant as stated in the claims since there is a need for some kind of surfactant modifier to lower the amount of surfactant. Furthermore, U.S. Pat. No. 4,712,239 describes multicomponent systems for use in pharmaceutical products, which systems comprising an oil, a nonionic surfactant with a hydrophilic-lipophilic balance above 8 and a cosurfactant which is a partial ether or ester of a polyhydroxyl alcohol and a $(C_{6-22})$fatty alcohol or acid. Optionally an aqueous phase is used and the therapeutic agent may be lipophilic or hydrophilic. Such systems are said to give enhanced transdermal delivery characteristics. In example 1, formulations X and XI contain isopropanol which make the formulations inappropriate for parenteral administration. Furthermore, it is to be noted that in example 1, formulation I the ratio of the medium-chain triglyceride to the caprylic-capric acid glycerol partial esters is 1:1.5. Also WO 93/02664 describes a microemulsion but it is in the form of a water-in-oil microemulsion. Among others it includes a water-soluble therapeutic agent. In EP 334 777 a microemulsion for parenteral or oral administration of cosmetics or pharmaceuticals is disclosed consisting of one polar and one lipid phase and using a mixture of surfactants based upon polyethylene glycol and polyglycerol. The amount of surfactants has to be above 15% by weight in order to achieve a microemulsion according to the definition above.

None of the prior art documents discloses a non-toxic microemulsion suitable for parenteral administration of substances having a low solubility in water, which microemulsion could be either in form of a oil-in-water microemulsion or a bicontinous microemulsion and also is easy to prepare. Thus, there is a need for a new vehicle having the above listed characteristics.

BRIEF DESCRIPTION OF THE INVENTION

The object of the present invention is to provide a pharmaceutically acceptable non-toxic vehicle which increases the solubility of compounds having a low solubility in water, and which vehicle is in form of a microemulsion which is stable, translucent and suitable for parenteral as well as oral and transdermal administration of one or more active compounds.

BRIEF DESCRIPTION OF THE FIGURE

FIG. 1 illustrates an experimental procedure according to the present invention.

DETAILED DESCRIPTION OF THE INVENTION

According to the present invention a microemulsion which is suitable for parenteral as well as oral and transdermal administration of one or more active compounds is disclosed. It has surprisingly been found that by using at least two types of modifiers it is possible to minimize the amount of the surfactant and thus, also the toxicity is minimized.

The present microemulsion comprises
- a polar phase containing water and optionally an agent for obtaining isotonic conditions, and one or more components (modifiers) for adjusting the polarity,
- a surfactant film modifier,
- a non-polar phase consisting of at least one pharmaceutically acceptable oil and
- a mixture of a hydrophilic and a hydrophobic surfactant up to 15% by weight of the total microemulsion, preferably 4–12%.

The polar phase includes water and optionally an agent for obtaining isotonic conditions, e.g. a NaCl— or glycerol solution. The polar phase also includes compound/compounds which decrease the polarity of the polar phase and thus, lowering the amount of surfactant. These compounds are called modifiers. Examples of modifiers are; polyethylene glycol 400 (PEG 400), polyethylene glycol 300 (PEG 300), polyethylene glycol 200 (PEG 200); propylene glycol; glucofurol (polyethyleneglycol tetrahydrofurfurylether); glycerol; sorbitol; mannitol; monosaccharides; disaccharides; dimethyl acetamide; solketal; methylpyrrolidone; 1-hydroxyethyl-2-pyrrolidon or hydroxyethyl lactamide. Preferred modifiers are one or more of the following; polyethylene glycol 400 (PEG 400), polyethylene glycol 300 (PEG 300), polyethylene glycol 200 (PEG 200); propylene glycol; glucofurol; glycerol; sorbitol; mannitol; monosaccharides or disaccharides. More preferred modifiers are one or more of the following; polyethylene glycol 400 (PEG 400), polyethylene glycol 300 (PEG 300), polyethylene glycol 200 (PEG 200); propylene glycol; glucofurol and glycerol. Most preferred modifier is the compound PEG 400.

The surfactant film modifier will be partially incorporated in the polar part of the surfactant film, thereby both increasing the area per lipid polar head group, and thus changing the spontaneous curvature of the lipid layers from being slightly curved toward water to become more planar or curved toward oil, and decreasing the stability of the lamellar liquid crystalline phase. Preferably the surfactant film modifier is ethanol, but also $C_3$-alcohols might be useful in case of transdermal administration.

The non-polar phase consists of at least one pharmaceutically acceptable oil which may be a triglyceride containing fatty acids having 4–18 carbon atoms; a diester of propylene glycol containing fatty acids having 4–18 carbon atoms; a monoester of a fatty acid containing an alcoholic part consisting of 1–5 carbon atoms and a fatty acid part having 8–22 carbon atoms or mixtures thereof.

Preferably the non-polar phase consists of a triglyceride containing at least 70% of fatty acids having 8–10 carbon atoms; a diester of propylene glycol containing at least 70% of fatty acids having 8–10 carbon atoms; or of a monoester of a fatty acid such as isopropylmyristate, isopropylpalmitate or ethyloleate or mixtures thereof. More preferred the non-polar phase consists of a triglyceride containing at least 70% of fatty acids having 8–10 carbon atoms; a diester of propylene glycol containing at least 70% of fatty acids having 8–10 carbon atoms or of isopropylmyristate. Most preferred the non-polar phase consists of either a triglyceride containing at least 70% of fatty acids having 8–10 carbon atoms or isopropylmyristate.

The hydrophobic surfactant is one of lecithin, sphingolipids and galacto lipids. Most preferred hydrofobic surfactant is purified soybean lecithin, comprising at least 90% phosphatidyl cholin. The non-ionic hydrophilic surfactant could be ethoxylated castor oil; ethoxylated fatty esters; sucrose fatty esters; mono-, di- and triesters of sorbitol and sorbitan and polyoxyethylene derivatives thereof; alkyl glucosides or alkyl polyglucosides; ethoxylated mono-hydroxy stearic acid and bile salts. Preferably the hydrophilic surfactant is polyethylene glycol (15)-12-hydroxy stearate, an alkylmaltoside, bile salts or mixtures thereof.

The present invention provides both an oil-in-water microemulsion and a bicontinous emulsion. By changing the ratio between the polar and the non-polar phase and also the amount of the modifiers mixed with the water in the polar phase, it is possible to obtain a microemulsion either in an oil-in-water type or bicontinous type. The microemulsion according to present invention may be used for solubilizing active compounds for intravenous, intraperitonial or intraarterial administration. It may also be used for preparations of active compounds having a low solubility in water for subcutaneous, intramuscular or transdermal administration. A further use of the microemulsion could be solubilization and increased absorption of active compounds having a low solubility in water when administed orally.

The active compound could e.g. be a proton pump inhibitor, calcium channel blocker, beta blocker, anesthetic, steroid, antioxidant, renin inhibitor, alkaloid, cytostatica, anti-coagulant, lipid regulating agent, anti-depressant, neuroleptic, immunosuppressant, immunomodulator, antibiotic, anti-inflammatory agent.

PREPARATION

The microemulsion could be prepared by mixing the components together in no particular order and allow the mixture to equilibrate typically two or three days. The equilibrating procedure could be shortened by gentle heating of the mixture to about 40° C., and stirring or shaking the mixture at regular intervals. It should be noted that the optimum concentration of the modifiers may have to be optimized for different batches of soybean lecithin and also for different active compounds.

The invention is illustrated more in detail by the following examples.

EXAMPLE 1

The following components were mixed together in a glass vial:

| Component | Composition | Amount (g) | wt % |
|---|---|---|---|
| 1a | | | |
| Surfactants | Epicuron 200[1] | 0.28 | 7.0 |
| | Soluthol HS15[2] | 0.196 | 4.9 |
| Aq-phase | water | 1.11 | 27.8 |
| | PEG 400[3] | 0.456 | 11.4 |
| | ethanol (99.5%) | 0.196 | 4.9 |
| oil phase | Miglyol 810[4] | 1.76 | 44.0 |
| 1b | | | |
| Surfactants | Epicuron 200[1] | 0.7 | 7.0 |
| | Soluthol HS15[2] | 0.49 | 4.9 |
| Aq-phase | water | 1.66 | 16.6 |
| | PEG 400[3] | 0.685 | 6.85 |
| | ethanol (99.5%) | 0.293 | 2.93 |
| oil phase | Miglyol 810[4] | 6.17 | 61.7 |

-continued

| Component | Composition | Amount (g) | wt % |
|---|---|---|---|
| 1c | | | |
| Surfactants | Epicuron 200[2] | 0.28 | 7.0 |
| | Soluthol HS15[2] | 0.196 | 4.9 |
| Aq-phase | 0.9% NaCl | 1.11 | 27.8 |
| | PEG 400[3] | 0.456 | 11.4 |
| | ethanol (99.5%) | 0.196 | 4.9 |
| oil phase | Miglyol 810[4] | 1.76 | 44.0 |
| 1d | | | |
| Surfactants | Epicuron 200[1] | 0.70 | 7.0 |
| | Soluthol HS15[2] | 0.49 | 4.9 |
| Aq-phase | 0.9% NaCl | 1.66 | 16.6 |
| | PEG 400[3] | 0.685 | 6.85 |
| | ethanol (99.5%) | 0.293 | 2.93 |
| oil phase | Miglyol 810[4] | 6.17 | 61.7 |

[1]Epicuron 200 is a purified soybean lecithin manufactured by Lucas Meyer, Germany.
[2]Soluthol HS15 is a polyoxyethylene glycol(15)-12-hydroxy stearat manufactured by BASF, Germany.
[3]PEG 400 is polyethylene glycol with the average molecular weight of 400 g/mole.
[4]Miglyol 810 is a triglyceride with the chainlength distribution of the fatty acids according to the manufacturer: $C_{6:0}$ = 2% max, $C_{8:0}$ = 70–80%, $C_{10:0}$ = 18–28%, $C_{12:0}$ = 2% max.

The glass vial was sealed and the mixture was shaken using a vortex mixer for a given number of minutes and then kept in a water bath keeping a constant temperature of 37° C. for two days. The vial was shaken using the vortex mixer two or three times a day. After two days the mixture appeared as a transparent slightly viscous one phase liquid. The mixture was kept at 25° C. for one week and showed no sign of phase separation. The sample was tested by visual appearance and using cross polarized filters to detect any sign of liquid crystalline phases. The temperature was raised to 37° C. and the sample was inspected after two days using the same procedure without any sign of phase separation. The sample was then kept in room temperature and inspected at regular intervals and the stability was at least six months.

EXAMPLE 2

The following components were mixed together in a glass vial:

| Component | Composition | Amount (g) | wt % |
|---|---|---|---|
| 2a | | | |
| Surfactants | Epicuron 200 | 0.120 | 3.0 |
| | Solutol HS15 | 0.240 | 6.0 |
| Aq-phase | water | 1.274 | 31.8 |
| | PEG 400 | 0.385 | 9.6 |
| | ethanol | 0.165 | 4.1 |
| Oil phase | isopropylmyristate | 1.828 | 45.6 |
| 2b: | | | |
| Surfactants | Epicuron 200 | 2.8 | 2.8 |
| | dodecylmaltocid | 1.2 | 1.2 |
| Aq-phase | water | 38.17 | 38.17 |
| | glucose | 9.58 | 9.58 |
| | ethanol | 10.08 | 10.08 |
| Oil phase | isopropylmyristate | 38.17 | 38.17 |
| 2c: | | | |
| Surfactants | Epicuron 200 | 4.9 | 4.9 |
| | dodecylmaltocid | 2.1 | 2.1 |
| Aq-phase | water | 35 | 35 |
| | glucose | 10 | 10 |
| | ethanol | 13 | 13 |
| Oil phase | isopropylmyristate | 35 | 35 |
| 2d: | | | |
| Surfactants | Epicuron 200 | 6.5 | 6.5 |
| | Na-taurocholate | 1.0 | 1.0 |
| Aq-phase | water | 39.25 | 39.25 |
| | PEG 400 | 7.0 | 7.0 |
| | ethanol | 7.0 | 7.0 |
| Oil phase | isopropylmyristate | 39.25 | 39.25 |
| 2e: | | | |
| Surfactants | Epicuron 200 | 6.5 | 6.5 |
| | Na-taurocholate | 1.0 | 1.0 |
| Aq-phase | water | 38.75 | 38.75 |
| | ethanol | 7.0 | 7.0 |
| Oil phase | isopropylmyristate | 39.25 | 39.25 |

The mixture was equilibrated according to the process in example 1, and after two days the mixture appeared as a transparent slightly viscous one phase liquid. The mixture was kept at 25° C. for one week and showed no sign of phase separation. The sample was tested by visual appearance and using cross polarized filters to detect any sign of liquid crystalline phases. The temperature was raised to 37° C. and the sample was inspected after two days using the same procedure without any sign of phase separation.

EXAMPLE 3

A microemulsion according to example 1 was prepared and the solubility of two sparingly soluble substances, felodipine (ethyl methyl 4-(2,3-dichlorophenyl)-1,4-dihydro-2,6-dimethyl-3,5-pyridinedicarboxylate) and cis-4b,5,9b,10-tetrahydro-4b,7,9,9b-tetramethyl-8-ethoxy-indeno(1,2-b)indole, hereinafter called the indeno indole, were tested. Different amounts of the substances were added to 1 ml samples of the microemulsion placed in glass vials. The samples were rotated for 48 hours to allow a complete wetting of the solid substance. The samples were than kept in a waterbath at 25° C. for at least one week before inspection. The samples were inspected for any solid substance or phase separation and the maximum solubility was defined as the range between the last sample in each series without any trace of solids or phase separation, and the first sample with remaining and undissolved substance or a phase separation.

TABLE 1

Solubility of felodipine and the indole in a microemulsion prepared according to example 1.

| | Sol. in water mg/l | sol. in microemulsion 1a mg/l | sol. in microemulsion 1b mg/l |
|---|---|---|---|
| Felodipine | 0.8 | 5000–10000 | 10000–15000 |
| The indeno indole | 2.0 | 40000–50000 | 60000–75000 |

EXAMPLE 4

The effect of a microemulsion according to example 1a on different pharmacological parameters in consious rats was compared with a 50% PEG 400/water solution using saline as a control.

Biological Effect

Experimental Procedure and Material

Animals

Adult, male Sprague-Dawley rats from Denmark, were used. After arrival at Astra Hässle AB, the animals were allowed at least one week to acclimatise before surgery. They were maintained in standard rat cages with aspen-chip bedding in a room with regulated temperature (20–22° C.), humidity (50–70%) and with a 12/12 h light/dark cycle. The animals had free access to pellets and to tap-water from bottles.

Surgery

The day before the experiments, the animals were anesthetised with Methohexital Sodium (Brietal, Lilly, Indianapolis, Ind., USA) 60 mg/kg i.p. and catheters were inserted in the right jugular vein (PE 25 for i.v. drug injections) and the tail artery (8 cm long PE 10 connected to PE 90 for blood pressure recordings). The tip of the arterial catheter was placed in the abdominal aorta below the renal arteries. ECG electrodes were placed under the skin over the apex and the right shoulder, and the ground electrodes were placed over the lumbar spine. This corresponds to a CR-recording. After the surgical procedure the animal was placed alone in a cage in a room with regulated humidity, temperature and light/dark cycle. The rats were also connected to a swivel system (Carnegie, Stockholm, Sweden), which delivered 1.0 ml sterile saline per hour via the arterial pressure line.

Hemodynamic and ECG Recordings

The day after the acute surgical procedure, the experiments were performed with the conscious rat residing in its own cage. The tail artery catheter was connected via a swivel allowing the animal to move relatively freely. The arterial pressure catheter was connected to a pressure transducer. The catheter was kept patent by slow infusion of 1.0 ml NaCl/h via a side tube of the arterial pressure line. The side tube was a 60 cm long PE 10 catheter, which has a high internal resistance. Thus, the side tube does not damp out arterial pulsations. Heart rate (HR) was measured from the undamped arterial pressure signal with a rate meter, and mean arterial pressure (MAP) was obtained by electronic filtering. The parameters from 4 animals were displayed simultaneously on a Grass polygraph (model 7 D). The ECG electrodes were connected intermittently to a Grass (7P6) ECG pre-amplifier. The ECG was recorded on a calibrated Siemens Elema Inkjet recorder.

The mean arterial pressure and heart rate signals were fed into a Datatranslation (DT 2801) AD converter placed in a Compaq 386SX computer. The computer program PC-LAB (written by Jan Axenborg and Ika Hirsch, AB Astra Hässle) sampled values of arterial pressure and heart rate repeatedly during the course of the experiments. The program sampled arterial pressure and heart rate for 20 s and calculated the average values of each 20 s period once every minute during the 4.5 h of experiments (i.e. created a file with 285 values of the individual parameters from 3–4 rats simultaneously).

In addition, the PC-LAB program sampled the ECG from all 4 rats 8 times during the course of the experiment (see FIG. 1). ECG signals were sampled at 800 Hz for 4 s, i.e. about 20 ECG cycles from each rat were stored in the computer memory. This array of samples from 4 rats was then transferred to a VAX-computer at AB Astra Hässle and was analysed with the PC-LAB program (written by Jan Axenborg). The PC-LAB. program calculated an average ECG from about 20 cycles. The 2nd cycle is the triggering cycle and is used for all calculations. From the average ECG, we calculated the PQ-time and QRS-duration in milliseconds.

Experimental Procedures

The experimental procedure is illustrated in FIG. 1. The experiment was performed on 3 different vehicles.

The basic hemodynamic parameters were recorded for 30 min. (see FIG. 1). Then the animals received 3 infusions of the vehicle given during 5 min. The volume was 0.3, 1 and 3 ml/kg for saline and PEG 400 and 0.15, 0.5 and 1.5 ml/kg for the microemulsion. The infusions were given 60 min. apart.

Blood samples for acid-base balance and blood gas determinations were obtained twice (before the first dose and at the end of the experiment).

ECG was obtained at intervals shown in FIG. 1.

Calculations and Statistics

Arterial Blood Pressure and Heart Rate Data

The data for each animal (n=6 for all experiment except heart rate data for PEG 400 (50%) where n=5) were normalized using the mean of the first three data points as a baseline and the deviation from this baseline for each datapoint was calculated. The two vehicles were compared by calculating the mean difference between each vehicle (PEG 400 (50%) or microemulsion) and the control (saline). A 95% confidence interval using the pooled variances and the t-distribution compensated for consecutive measurements with the Bonferoni technique for the data points immediately after each infuson was calculated.

ECG, Acid-base Balance, Blood Gases and Plasma Elecrolytes

The results are presented as mean values and the variability is expressed as SEM (n=6).

Results and Conclusions

A microemulsion according to example 1a was compared with a 50% aqueous solution of PEG 400 which is a co-solvent often used for intravenous administration. Saline was used as a control. The results are shown in tables 1–3. The data shows that it is possible to administrate, by intravenous infusion to concious rats, a microemulsion according to example 1a up to 0.5 ml/kg without causing any significant effect on acid-base balance, blood gases, plasma electrolytes, heart rate or PQ time. There is a significant but very small decrease in the arterial blood pressure immediately after the second dose but this is considered to be of no biological relevance.

At the highest dose, 1.5 ml/kg (microemulsion) and 3.0 ml/kg (PEG 400 (50%), the effect of the microemulsion and PEG 400 solution was very similar. A small increase in arterial blood pressure, for the microemulsion only, and a moderate bradycardic effect together with a temporary prolongation of the PQ time for both vehicles.

The solubility of felodipine and the indenoindol used in example 3 in PEG 400 (50%) are 0.7 mg/ml and 0.2 mg/ml respectively. Using the microemulsion it is thus possible to administrate 5 times more of felodipine and over 100 times more of the indenoindol compared to a 50% solution PEG 400. The microemulsion is surprisingly superior compared to The PEG 400 solution for solubilization and administration of compounds with a low solubility in water.

TABLE 1a

Arterial blood pressure (mm Hg)

| Time (min) | −25.5 | −15.5 | −5.5 | 4.5 | 14.5 | 24.5 | 34.5 | 44.5 | 54.5 | 64.5 | 74.5 | 84.5 | 94.5 | 104.5 | 114.5 | 124.5 | 134.5 | 144.5 |
|---|---|---|---|---|---|---|---|---|---|---|---|---|---|---|---|---|---|---|
| Peg 400-sal | −0.4 | 1.9 | −2.7 | 0.8 | 1.2 | 4.7 | 2.2 | −1.8 | 0.4 | 3.6 | 5.9 | 5.9 | 2.9 | 2.4 | 0.8 | 5.5 | 0.3 | 0.7 |
| Conf. int. (95%) | | | | +−6.0 | | | | | | +−10.4 | | | | | | +−10.6 | | |
| Microem.-sal | 2.8 | −1.2 | −1.4 | 2.5 | −1.7 | 5.3 | 6.2 | −0.7 | −0.3 | 6.6 | 3.6 | 4.5 | 4.3 | 1.4 | 4.1 | 13.0 | 3.5 | 8.9 |
| Conf. int (95%) | | | | +−5.3 | | | | | | +−8.6 | | | | | | +−8.7 | | |

TABLE 1b heart rate (beats/min)

| Time(min) | −25.5 | −15.5 | −5.5 | 4.5 | 14.5 | 24.5 | 34.5 | 44.5 | 54.5 | 64.5 | 74.5 | 84.5 | 94.5 | 104.5 | 114.5 | 124.5 | 134.5 | 144.5 |
|---|---|---|---|---|---|---|---|---|---|---|---|---|---|---|---|---|---|---|
| Peg 400-sal | 0.2 | 13.7 | 3.2 | −15.2 | −2.5 | 11.3 | 2.7 | −5.5 | 4.6 | −20.3 | 4.3 | −1.9 | 1.6 | 4.5 | 0.6 | −43.7 | −26.9 | 0.3 |
| Conf. int. (95%) | | | | +−8.7 | | | | | | +−20.4 | | | | | | +−15.4 | | |
| Microem.-sal | 8.0 | 7.0 | 6.9 | −12.3 | −10.1 | 21.9 | 20.9 | −5.0 | 4.8 | −24.7 | −13.3 | 7.1 | 19.9 | 16.7 | 18.5 | −36.9 | −16.1 | 18.8 |
| Conf. int. (95%) | | | | +−13.9 | | | | | | +−23.0 | | | | | | +−20.4 | | |

TABLE 2

PQ-time (msec)

| Time(min): | 29 | 36 | 59 | 66 | 119 | 126 | 155 |
|---|---|---|---|---|---|---|---|
| Saline: | 45.8 | 43.7 | 45.3 | 45.5 | 46.0 | 45.1 | 47.0 |
| SEM: | 0.99 | 0.86 | 0.86 | 0.68 | 1.02 | 0.40 | 0.95 |
| PEG 400 (50%): | 45.3 | 45.3 | 44.7 | 46 | 44.2 | 51 | 46.3 |
| | 1.42 | 1.48 | 1.57 | 1.51 | 1.37 | 2.11 | 1.71 |
| Microemulsion: | 46.2 | 47.3 | 46.5 | 49 | 44.5 | 51 | 44.5 |
| SEM: | 1 | 0.68 | 1.04 | 0.98 | 1.1 | 1.77 | 0.81 |

TABLE 3

Acid-base balance, blood gases and plasma electrolytes.

| | pH | | pCO2 (kPa) | | pO2 (kPa) | | BE (mmol/L) | | Na (mmol/L) | | K (mmol/L) | |
|---|---|---|---|---|---|---|---|---|---|---|---|---|
| Time (min): | 0 | 155 | 0 | 155 | 0 | 155 | 0 | 155 | 0 | 155 | 0 | 155 |
| Saline | 7.49 | 7.49 | 4.45 | 4.93 | 12.13 | 12.08 | 2.73 | 4.42 | 142.83 | 140.67 | 3.47 | 3.73 |
| SEM | 0.01 | 0.01 | 0.18 | 0.20 | 0.12 | 0.25 | 0.62 | 1.10 | 0.75 | 0.21 | 0.40 | 0.14 |
| PEG 400 (50%) | 7.47 | 7.47 | 4.37 | 4.39 | 11.93 | 12.06 | 0.83 | 0.85 | 143.67 | 142.83 | 3.00 | 3.07 |
| SEM | 0.01 | 0.01 | 0.09 | 0.10 | 0.24 | 0.35 | 0.59 | 0.56 | 0.88 | 0.70 | 0.14 | 0.15 |
| Microemulsion | 7.47 | 7.47 | 4.91 | 4.24 | 11.48 | 11.13 | 3.12 | 0.58 | 141.50 | 143.33 | 3.32 | 2.93 |
| SEM | 0.01 | 0.01 | 0.23 | 0.18 | 0.62 | 0.73 | 1.09 | 0.57 | 1.18 | 0.80 | 0.27 | 0.13 |

What is claimed is:

1. A non-toxic oil-in-water or bicontinuous microemulsion as a vehicle for administration of at least one pharmaceutically active ingredient comprising:
   (a) a polar phase comprising water and at least one component for adjusting the polarity of the polar phase;
   (b) a surfactant film modifier in the amount of about 2.93% to about 13% by weight of the total emulsion, wherein the surfactant film modifier is a monohydric alcohol with 2–3 carbon atoms;
   (c) a non-polar phase comprising at least one pharmaceutically acceptable oil; and
   (d) a mixture of a hydrophilic surfactant and a hydrophobic surfactant up to 15% by weight of the total microemulsion, wherein the hydrophobic surfactant is selected from the group consisting of lecithin, sphingolipids and galacto lipids.

2. The microemulsion according to claim 1, wherein the component for adjusting the polarity of the polar phase is selected from the group consisting of polyethylene glycol, propylene glycol, glucofurol, glycerol, sorbitol, mannitol, monosaccharides, disaccharide, dimethyl acetamide, solketal, methylpyrrolidone, 1-hydroxyethyl-2-pyrrolidone, hydroxyethyl lactamide and mixtures thereof.

3. The microemulsion according to claim 2, wherein the component for adjusting the polarity of the polar phase is selected from the group consisting of polyethylene glycol, propylene glycol, glucofurol, glycerol, sorbitol, mannitol, monosaccharides, disaccharides and mixtures thereof.

4. The microemulsion according to claim 1, wherein the polar phase further comprises an agent for obtaining isotonic conditions.

5. The microemulsion according to claim 1, wherein the surfactant film modifier is ethanol.

6. The microemulsion according to claim 1, wherein the pharmaceutically acceptable oil in the non-polar phase is selected from the group consisting of a triglyceride containing 4–18 carbon atoms, a diester of propylene glycol containing fatty acids having 4–18 carbon atoms, a monoester of fatty acid containing an alcoholic part consisting of 1–5 carbon atoms, a fatty acid part having 8–22 carbon atoms and mixtures thereof.

7. The microemulsion according to claim 6, wherein the pharmaceutically acceptable oil in the non-polar phase is selected from the group consisting of a triglyceride containing at least 70% of fatty acids having 8–10 carbon atoms, a diester of propylene glycol containing at least 70% of fatty acids having 8–10 carbon atoms, a monoester and mixtures thereof.

8. The microemulsion according to claim 7, wherein the pharmaceutically acceptable oil in the non-polar phase is selected from the group consisting of a triglyceride containing at least 70% of fatty acids having 8–10 carbon atoms, isopropylmyristate and mixtures thereof.

9. The microemulsion according to claim 1, wherein the hydrophobic surfactant is purified soybean lecithin comprising at least 90% phosphatidyl chloine.

10. The microemulsion according to claim 1, wherein the hydrophilic surfactant is selected from the group consisting of ethoxylated castor oil, ethoxylated fatty esters, sucrose fatty esters, mono-, di-, and triesters of sorbitol or sorbitan and polyethylene derivatives thereof, alkyl glucosides, alkyl polyglucosides, ethoxylated mono-hydroxy steric acid, bile salts, and mixtures thereof.

11. A microemulsion according to claim 10, wherein the hydrophilic surfactant is selected from the group consisting of polyethylene glycol(15)-12-hydroxy stearate, alkylmaltoside, bile salts and mixtures thereof.

12. A microemulsion according to claim 1, wherein the amount of surfactant is 4–12% by weight of the total micro emulsion.

13. A process for the preparation of the microemulsion according to claim 1 comprising the steps: (a) mixing the components together in no particular order and (b) allowing the mixture to equilibrate.

14. The microemulsion according to claim 4, wherein the agent for obtaining isotonic conditions is a NaCl solution or a glycerol solution.

15. The process according to claim 13, wherein the equilibrating step (b) is shortened by gentle heating of the mixture at about 40° C. and stirring or shaking the mixture at regular intervals.

16. A pharmaceutical formulation comprising at least one pharmaceutically active ingredient and the microemulsion according to claim 1.

17. The pharmaceutical formulation according to claim 16, wherein the pharmaceutically active ingredient is selected from the group consisting of a proton pump inhibitor, calcium channel blocker, beta blocker, anesthetics, steroid, antioxidant, renin inhibitor, alkaloid, cytostatica, anticoagulant, lipid regulating agent, antidepressant, neuroleptic, immunosuppressant, immunomodulator, antibiotic and an antiinflammatory agent.

18. The pharmaceutical formulation according to claim 17, in a form suitable for parenteral administration.

19. The pharmaceutical formulation according to claim 17, in a form suitable for oral administration.

20. The pharmaceutical formulation according to claim 17, in a form suitable for transdermal administration.

21. The microemulsion according to claim 2 or 3, wherein the polyethylene glycol is selected from the group consisting of polyethylene glycol 200, polyethylene glycol 300 or polyethylene glycol 400.

22. The microemulsion according to claim wherein 21, the polyethylene glycol is polyethylene glycol 400.

* * * * *

UNITED STATES PATENT AND TRADEMARK OFFICE
CERTIFICATE OF CORRECTION

PATENT NO. : 6,602,511 B2
DATED : August 5, 2003
INVENTOR(S) : von Corswant

It is certified that error appears in the above-identified patent and that said Letters Patent is hereby corrected as shown below:

<u>Title page,</u>
Item [86], delete "Sep. 20, 1996" and substitute therefor -- Sep. 30, 1996 --.
Item [56], References Cited, OTHER PUBLICATIONS, 1st reference, delete "defintion" and substitute therefor -- definition --.

<u>Column 1,</u>
Line 5, delete "3718" and substitute therefor -- 371 of --.
Line 51, delete "ect." and substitute therefor -- etc. --.

Signed and Sealed this

Ninth Day of December, 2003

JAMES E. ROGAN
*Director of the United States Patent and Trademark Office*